US 8,685,712 B2

(12) United States Patent
Okamoto

(10) Patent No.: US 8,685,712 B2
(45) Date of Patent: Apr. 1, 2014

(54) APPARATUS FOR PERFORMING BIOCHEMICAL PROCESSING USING A CONTAINER WITH A PLURALITY OF WELLS AND THE CONTAINER FOR THE APPARATUS

(75) Inventor: Hideaki Okamoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 897 days.

(21) Appl. No.: 11/540,568

(22) Filed: Oct. 2, 2006

(65) Prior Publication Data
US 2007/0077646 A1 Apr. 5, 2007

(30) Foreign Application Priority Data
Oct. 4, 2005 (JP) ................. 2005-291297

(51) Int. Cl.
*C12M 1/34* (2006.01)
*B01L 7/00* (2006.01)

(52) U.S. Cl.
CPC ....................... *B01L 7/00* (2013.01)
USPC .............. 435/287.2; 435/287.3; 435/288.4; 435/303.1; 435/305.3

(58) Field of Classification Search
USPC .................... 435/809, 287.2, 288.4
See application file for complete search history.

(56) References Cited

U.S. PATENT DOCUMENTS

| | | | | |
|---|---|---|---|---|
| 4,919,894 A | * | 4/1990 | Daniel | 422/104 |
| 5,496,517 A | * | 3/1996 | Pfost et al. | 422/63 |
| 5,567,617 A | * | 10/1996 | Caprio et al. | 435/287.2 |
| 5,721,136 A | | 2/1998 | Finney et al. | |
| 5,851,492 A | * | 12/1998 | Blattner | 422/102 |
| 6,197,572 B1 | * | 3/2001 | Schneebeli | 435/286.2 |
| 6,426,215 B1 | * | 7/2002 | Sandell | 435/305.3 |
| 6,518,060 B2 | * | 2/2003 | Heimberg et al. | 435/305.3 |
| 2005/0123445 A1 | * | 6/2005 | Blecka et al. | 422/64 |
| 2007/0077580 A1 | | 4/2007 | Ikeda et al. | 435/6 |
| 2007/0077648 A1 | | 4/2007 | Okamoto et al. | 435/303.1 |

FOREIGN PATENT DOCUMENTS

JP 7-107999 4/1995

OTHER PUBLICATIONS

Funakoshi General Catalog 2005-2006 for devices, Aug. 2005, pp. 16 and 18.

* cited by examiner

*Primary Examiner* — Michael Hobbs
(74) *Attorney, Agent, or Firm* — Fitzpatrick, Cella, Harper and Scinto

(57) ABSTRACT

A biochemical processing apparatus for performing biochemical processing in a container having a plurality of wells capable of holding liquid includes an opening/closing mechanism configured to open or close a lid capable of hermetically and selectively sealing the plurality of wells.

6 Claims, 9 Drawing Sheets

APPARATUS FOR PERFORMING BIOCHEMICAL PROCESSING USING A CONTAINER WITH A PLURALITY OF WELLS AND THE CONTAINER FOR THE APPARATUS

CLAIM OF PRIORITY

This application claims the benefit of Japanese Application No. 2005-291297 filed Oct. 4, 2005, which is hereby incorporated by reference herein in its entirety.

BACKGROUND OF THE INVENTION

1. Field of the Invention

The present invention relates to a biochemical processing apparatus, such as a deoxyribonucleic acid (DNA) testing apparatus, and to a container for the biochemical processing apparatus. In particular, the present invention relates to a configuration of a container for the amplification and purification of DNA samples and to an opening and closing mechanism for the container.

2. Description of the Related Art

For quickly and accurately analyzing the base sequence of a nucleic acid and detecting a target nucleic acid in nucleic acid samples, many methods based on hybridization reactions using a probe carrier, such as a DNA microarray, have been proposed. A DNA microarray is a collection of probes having a base sequence complementary to a target nucleic acid and attached to a solid surface, such as a bead or glass plate, at a high density. The detection of a target nucleic acid using the DNA microarray typically involves the following steps.

In the first step, the target nucleic acid is amplified by an amplification method, such as a polymerase chain reaction (PCR) method. Specifically, a first primer and a second primer are added to a nucleic acid sample, which is then subjected to temperature cycling in the presence of an enzyme. The first primer is specifically bound to part of the target nucleic acid, while the second primer is specifically bound to part of a nucleic acid complementary to the target nucleic acid. When a duplex nucleic acid containing the target nucleic acid is bound to the first and second primers, the duplex nucleic acid containing the target nucleic acid is amplified by an elongation reaction (hereinafter, this is referred to as "first PCR").

After the duplex nucleic acid containing the target nucleic acid is sufficiently amplified, components, such as non-reacted primers and nucleic acid fragments, other than the amplified duplex nucleic acid are removed by purification. Examples of known purification methods include a method of attaching a duplex nucleic acid to magnetic particles and a method using a column filter.

After the purification, a third primer is added to the purified nucleic acid sample, which is then subjected to temperature cycling. The third primer is labeled with an enzyme, fluorescent material, light-emitting material, or the like and specifically bound to part of a nucleic acid complementary to the target nucleic acid. When the third primer is bound to the nucleic acid complementary to the target nucleic acid, a labeled target nucleic acid is amplified by an elongation reaction (hereinafter, this is referred to as "second PCR").

As a result, if the target nucleic acid is contained in the nucleic acid sample, a labeled target nucleic acid is generated, while if the target nucleic acid is not contained in the nucleic acid sample, a labeled target nucleic acid is not generated.

In the second step, this nucleic acid sample is brought into contact with a DNA microarray so that a hybridization reaction between the nucleic acid sample and a probe on the DNA microarray takes place. If a target nucleic acid complementary to a probe is present, the probe and the target nucleic acid create a hybrid body.

The third step involves the detection of the target nucleic acid. The detection of whether a probe and a target nucleic acid have created a hybrid body can be made with a labeled material of the target nucleic acid. This allows a determination as to the presence of a specific base sequence.

Japanese Patent Laid-Open No. 7-107999 discloses an apparatus capable of independently and sequentially performing the multiple steps described above. This apparatus is configured such that a movable pipettor delivers necessary liquids to containers to allow reactions to take place.

A biochemical processing apparatus capable of performing a plurality of processing steps requires many spaces (containers) in which liquids are separately held. For example, such a biochemical processing apparatus requires containers which serve as holders for separately holding many reagents, and other containers which serve as reaction fields for performing biochemical processing.

A problem of contamination resulting from the transfer of liquid between such containers needs to be solved. Liquid often spatters, for example, when a pipetting device is used for the transfer of liquid. To solve this problem, it is preferable to configure the containers such that the transfer distance of liquid is reduced, that is, the containers are arranged in close proximity to each other.

This configuration is advantageous in that an area to be temperature-controlled is reduced, and that the size of a transfer device is reduced.

However, as the containers become closer to each other, the problem of contamination of reagents in adjacent containers grows.

There is another possible configuration in which the openings of the containers are covered with a film until immediately before use, and are opened as needed. However, the removal of the film causes liquid to evaporate during processing, such as PCR processing, which involves heating. Another problem is condensation which may occur during processing that involves cooling.

SUMMARY OF THE INVENTION

The present invention provides a biochemical processing apparatus having a simple configuration and capable of preventing contamination of liquids in holders, and a container for the biochemical processing apparatus.

According to an aspect of the present invention, a biochemical processing apparatus for performing biochemical processing in a container having a plurality of wells includes a retainer configured to retain the container, and a sealing mechanism configured to hermetically and selectively seal some of the plurality of wells.

According to another aspect of the present invention, a container having a plurality of wells arranged in a matrix form includes a lid configured to hermetically and selectively seal the plurality of wells, and a supporting member configured to support the lid such that the lid is movable between an opening position and a closing position.

Further features of the present invention will become apparent from the following description of exemplary embodiments with reference to the attached drawings.

DESCRIPTION OF THE EMBODIMENTS

Figure 1:
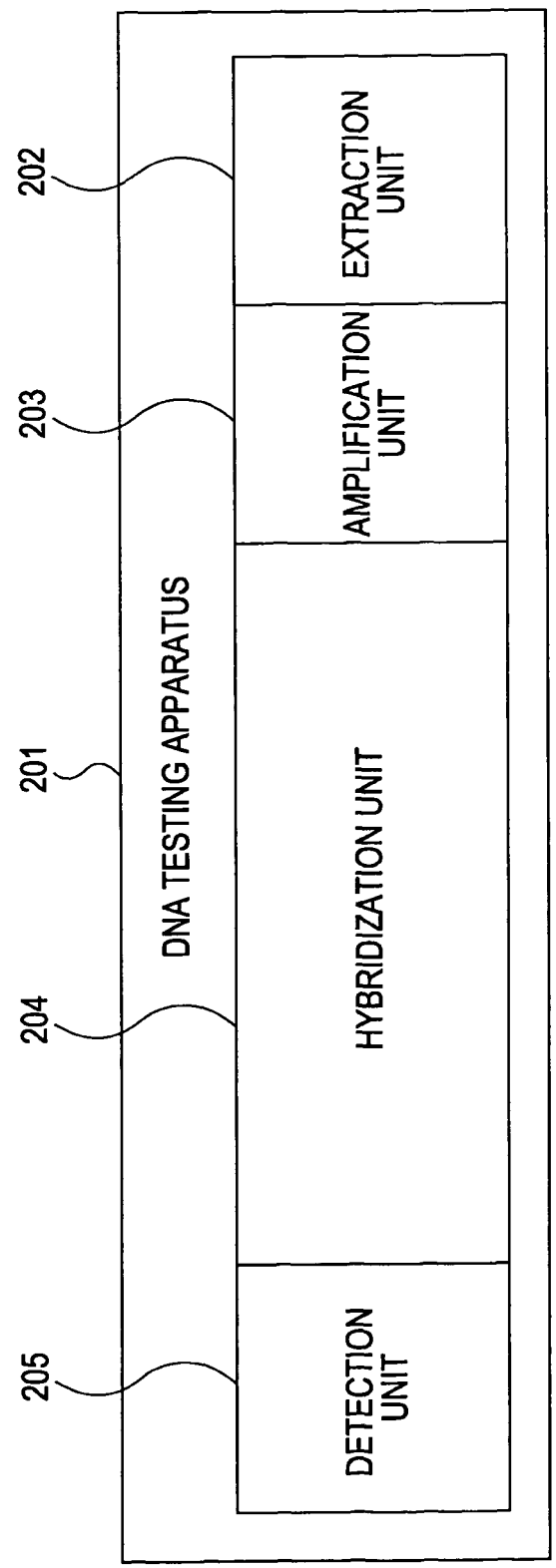
FIG. 1 is a schematic diagram illustrating a DNA testing apparatus of the present invention.

A DNA testing apparatus will be described in detail as an example of a biochemical processing apparatus of the present invention.

The DNA testing apparatus is an apparatus which independently and sequentially performs multiple steps that involve the amplification, hybridization, and detection of a DNA sample. The amplification step will be mainly discussed below.

A container used in the present embodiment is a container with a plurality of wells configured to hold liquid therein and has a movable lid serving as a closing unit.

The container may be a 96-well PCR microplate which is commercially available, or a collection of wells formed into a shape similar to that of the 96-well PCR microplate. The container is filled in advance with reagents to be used in PCR steps. Wells on one side of the container are used in performing first and second PCR steps, wells in the center of the container are used in purification, and wells on the other side of the container are filled with reagents to be used in purification and the first and second PCR steps.

It is preferable that a sealing member be fixed to the openings of the wells by bonding or welding. In the container, some wells are filled with reagents in advance, and the other wells are filled with solutions at the time of reaction. Since the sealing member seals off the interiors of all the wells from the outside until the reaction starts by attaching the wells to the apparatus, it is possible to prevent foreign matter from entering the wells. The sealing member is pierced by a piercing unit of the apparatus before solutions are drawn from or injected into the wells. Since the sealing member is pierced immediately before the use of the wells, the amount of time during which the interiors of the wells are exposed to the outside is minimized.

A movable lid made of elastic material is placed on the sealing member. The lid is large enough to at least hermetically seal the wells used in the first and second PCRs. The lid is constantly biased in a direction to hermetically seal the wells, and is supported by the container in a manner to be openable and closable about an axis. Therefore, for example, after the lid is opened to remove solutions from the wells upon completion of the first PCR, the wells can be sealed again as necessary. Since the lid is opened only when necessary, the amount of evaporation of the solutions and the possibility of accidental leakage of the solutions to the outside are extremely small. The lid is opened and closed by a drive unit of the apparatus. The mode of movement of the lid is not limited to the rotation described above. The lid may slide or vertically drop down to the openings of the wells.

In the DNA testing apparatus, components which perform the amplification step are broadly divided into the following units: a thermal cycling unit, a purifying unit, and a cold reserving unit. These three units are disposed in close proximity to one another so that their respective functions are carried out without moving the container.

The thermal cycling unit includes a thermal cycling block, Peltier devices, and a heater. The thermal cycling block is made of metal with high heat conductivity, such as aluminum or copper alloy, and provided with a plurality of holes into which the container is to be closely fitted. The number of the holes is the same as that of the wells in which the first and second PCRs are performed. The container is fitted into the thermal cycling block to allow the first and second PCRs to be performed. Generally, preset temperatures of about 92° C., 55° C., and 72° C. are sequentially maintained for respective predetermined time periods within one cycle, which is repeated about 40 times (in the first PCR) and about 25 times (in the second PCR).

It is preferable that the thermal cycling unit be provided with a heating unit above the container, that is, on the side where the lid is located. The heating unit includes a heating block made of metal with high heat conductivity, such as aluminum or copper alloy, Peltier devices, and a heater. The application of heat to the heating block allows the container to be heated from above through the lid. The heating block is sized to cover only the wells in which the first and second PCRs are performed and is configured not to allow cold reserving wells to be heated. Since this allows the inner wall temperatures of the wells to increase, evaporating and rising solutions are prevented from adhering to the inner walls and causing condensation.

The heating unit above the wells is located on the lid during the first and second PCRs. When solutions are injected into or drawn from the first and second PCR wells, or when the sealing member is pierced, the heating unit moves away from the original position so as not to interfere with such operation. The lid is configured to open when the heating unit moves away.

The purifying unit is disposed opposite the center portion of the container. A possible method of purification is to use magnetic particles supplied to wells in advance and a magnet placed near the wells.

Specifically, after a nucleic acid solution, a cleaning solution, ethanol, and the like are separately supplied to different wells and stirred, nucleic acid is attracted to the magnetic particles. Next, the magnet which is normally isolated from the wells is brought closer to the purifying wells. The magnetic particles with nucleic acid are thus held in one place. Then, solutions in the purifying wells are drawn therefrom while the magnetic particles with nucleic acid are left therein. Next, eluate is supplied to the purifying wells to separate the nucleic acid from the magnetic particles. By bringing the magnet closer to the purifying wells, the magnetic particles are brought into one place. Then, solutions in the purifying wells are drawn therefrom while the magnetic particles therein are left behind. By following this series of steps, a purified nucleic acid is obtained.

At the position where the container is attached to the apparatus, the thermal cycling unit and the cold reserving unit are disposed opposite each other. In other words, if the thermal cycling unit is disposed at one end of a well plate, the cold reserving unit is disposed at the other end of the well plate. The cold reserving unit includes a cooling block and Peltier devices. The cooling block is made of metal with high heat conductivity, such as aluminum or copper alloy, and provided with a plurality of holes into which the container is to be closely fitted. The number of the holes is at least the same as that of the wells filled with reagents. The cooling block is covered with a thermal insulator.

A pipetting unit is provided for transferring solutions among wells which are opposite the thermal cycling unit, cold reserving unit, and purifying unit. A removable pipette tip at the tip of the pipetting unit is replaced with a new one as required.

During the period from when the container is attached to the apparatus until the time when the container is actually used, reagents are stored in the cold reserving unit at temperatures which prevent the reagents from deteriorating. The storage temperature of the reagents ranges from about 4° C. to 20° C. The cold reserving unit has to maintain this temperature without being affected by the temperature (from 55° C. to 92° C.) of the thermal cycling unit near the cold reserving unit.

The purifying unit is arranged between the cold reserving unit and the thermal cycling unit so that the cold reserving unit and the thermal cycling unit are separated and so that their temperatures are prevented from affecting each other.

Since the thermal cycling unit, the cold reserving unit, and the purifying unit are arranged in this manner, the limited space of the PCR microplate can be effectively used. This not only facilitates the size reduction of the apparatus, but also reduces the moving distance of the pipetting unit for delivering and drawing solutions.

If the container is specified to be used only in the amplification and purification steps, the user can remove the container from the apparatus upon completion of these steps. The container can be discarded after being removed. The lid, which is integral with the container, can be discarded together. The lid may be configured to be integral with the apparatus. However, the lid integral with the container provides a simpler configuration, as there is no need for a mechanism of cleaning or replacing the lid. Even if the lid is configured to be cleanable or replaceable, it is still possible that a reactive residue contaminates a container to be used in the next test. The lid integral with the container is advantageous in this regard as well.

First Exemplary Embodiment

An exemplary amplification step of a DNA testing apparatus will be further described in detail.

FIG. 1 is a schematic diagram illustrating a DNA testing apparatus 201 of a first exemplary embodiment. The DNA testing apparatus 201 includes an extraction unit 202 for extracting DNA from a biological sample, an amplification unit 203 for amplifying the DNA, a hybridization unit 204 for binding the amplified DNA to a DNA probe, and a detection unit 205 for detecting whether the amplified DNA has been bound to a DNA probe. The testing process proceeds in order from extraction in the extraction unit 202, amplification in the amplification unit 203, hybridization in the hybridization unit 204, and to detection in the detection unit 205.

Figure 2:
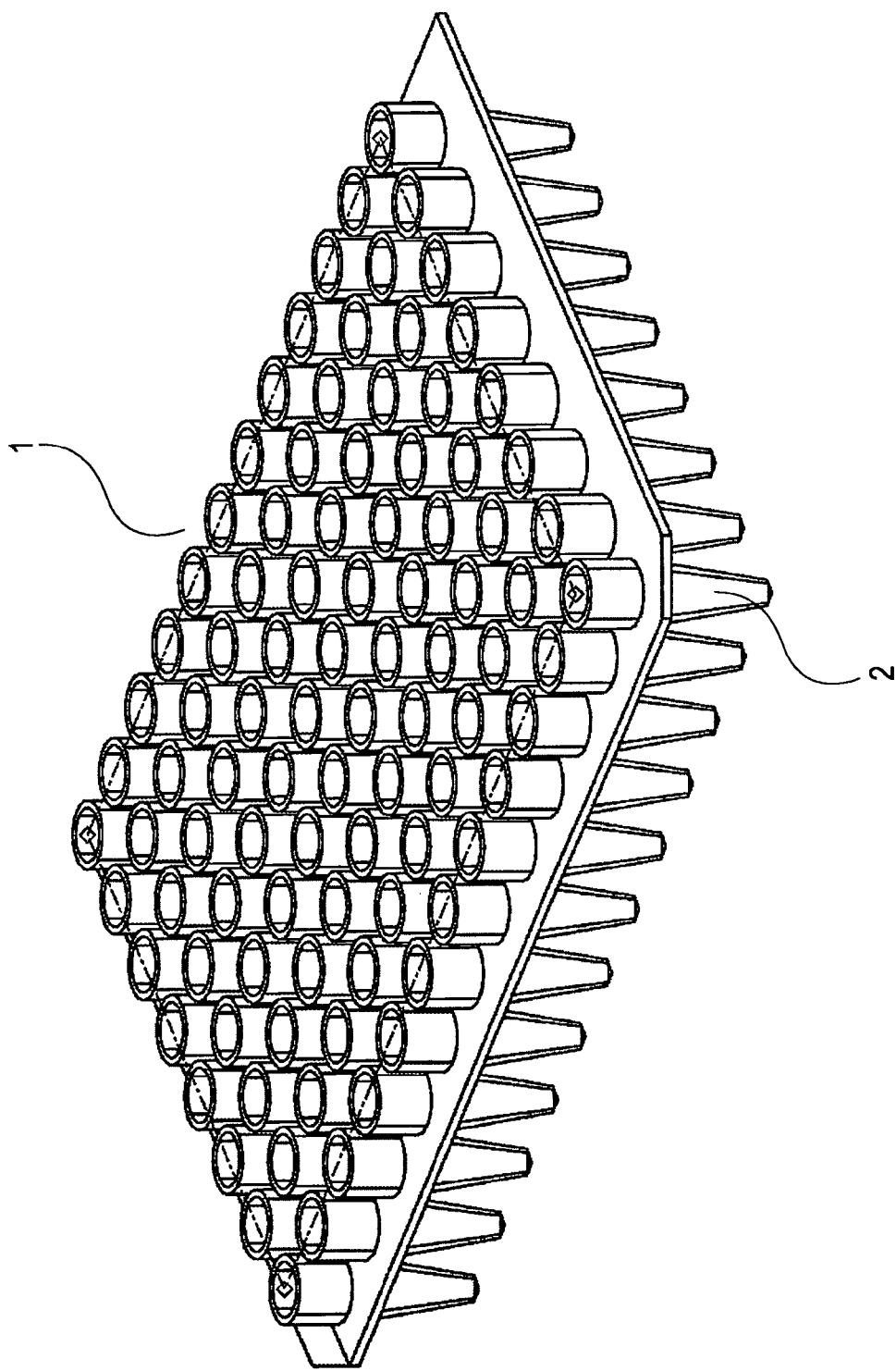
FIG. 2 is a perspective view illustrating a well portion of a container of the present invention.

FIG. 2 is a perspective view illustrating a well portion of a container. The well portion is composed of a polypropylene PCR microplate 1 which is commercially available, or is formed into a shape similar to that of the PCR microplate 1, in which 8×12 wells are arranged at a pitch of 9 mm. A tip (bottom) 2 of each well is formed to fit in a thermal cycling block and a cooling block, which are described below.

Figure 3:
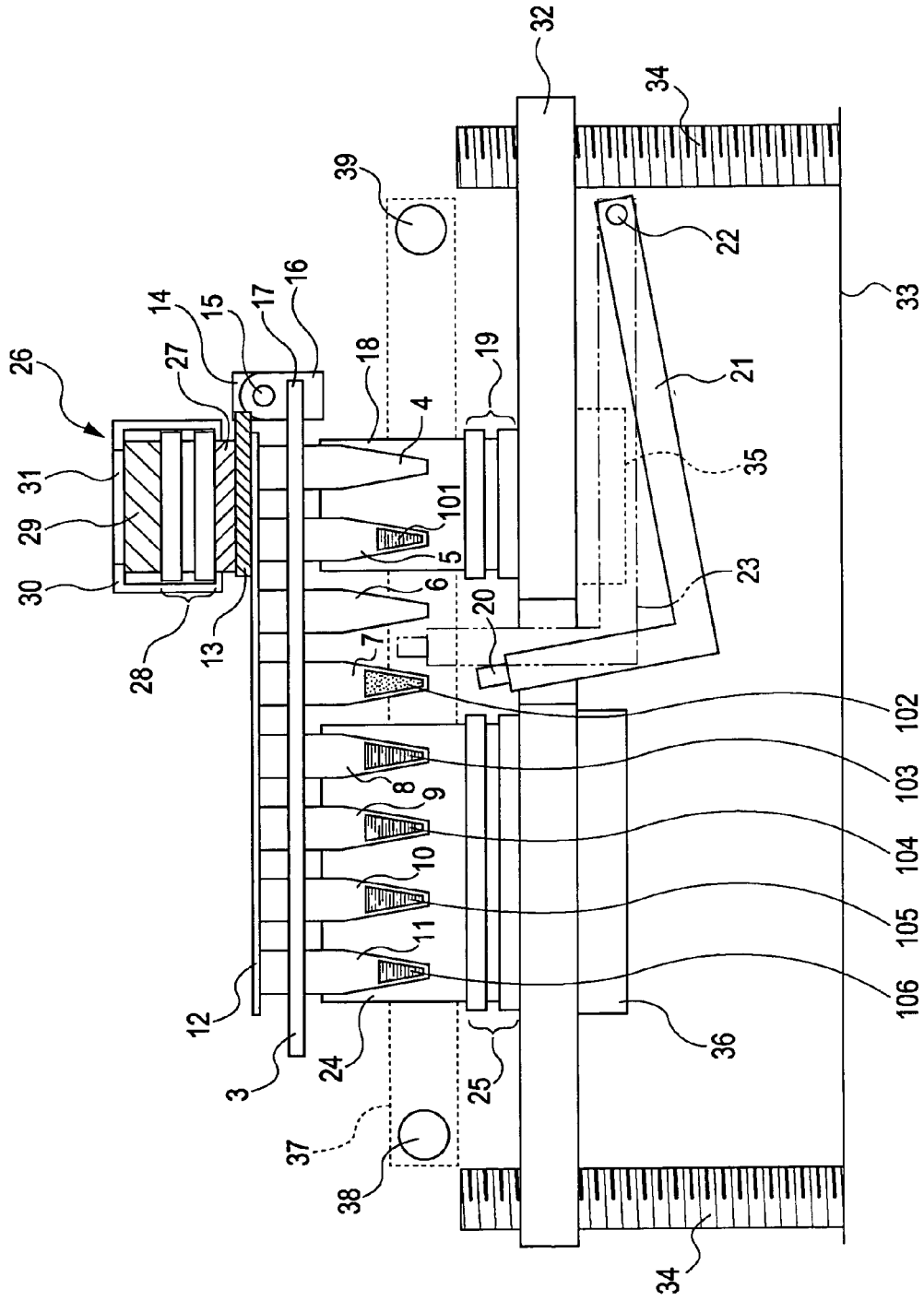
FIG. 3 is a front view illustrating an amplification unit of the DNA testing apparatus of the present invention.

FIG. 3 is a front view of the amplification unit 203 of the DNA testing apparatus 201 and illustrates the configuration of a container, well arrangement, and the positional relationship of a thermal cycling unit, a cold reserving unit, and a purifying unit. A state during first and second PCR reactions is illustrated in FIG. 3.

In a container 3, 8 by 12 wells are divided into 12 rows, each row having 8 wells. This allows 12 samples to be tested at the same time.

Wells illustrated in FIG. 3 will be described from the right side. Although the following description primarily refers to eight wells in one row, the same applies to wells in the other rows. A well 4 at the right end is for performing the second PCR and is initially empty. A well 5 is for performing the first PCR and is filled in advance with a solution 101, such as an enzyme reagent or a primer. Wells 6 and 7 are for performing purification and the well 7 is used first. The well 7 is filled with a magnetic particle solution 102 in advance, while the well 6 is empty. A well 8, a well 9, and a well 10 are filled in advance with a cleaning solution 103, ethanol 104, and eluate 105, respectively. A well 11 at the left end is filled in advance with a solution 106, such as a reagent or a primer used in the second PCR. The 12 rows of these wells are arranged in the direction perpendicular to the plane of the drawing.

The well arrangement is not limited to this and may be changed depending on the type of reagent. For example, 8 by 12 wells may be divided into 6 groups, each containing 2 rows by 8 wells, such that 6 samples can be tested at the same time. In this case, the first PCR may be performed in some wells in odd-numbered rows, the second PCR may be performed in some wells in even-numbered rows, and the other rows may be used in purification and to store reagents to be used in purification and the second PCR.

A laminated film 12 made of aluminum or the like is fixed to the openings of the 96 wells by bonding or welding. This prevents foreign matter from entering the wells. Before a solution is drawn from or injected into each well, the film 12 is pierced by a piercing cutter.

Since the film 12 is pierced by a cutter unit (not shown) immediately before the use of each well, the amount of time during which the solution and reaction field in the well are exposed to the outside can be minimized. Therefore, the possibility of the entrance of foreign matter into the well and the leakage of solution to the outside can be minimized.

A silicon rubber lid 13 and a lid retainer 14 for retaining the lid 13 are rotatably supported by a fulcrum shaft 15. A biasing member, such as a torsion coil spring (not shown), is attached to the fulcrum shaft 15 and biases the lid 13 and lid retainer 14 to hermetically seal the wells 4 and 5. A bearing 16 rotatably supports the fulcrum shaft 15. If a commercially available PCR microplate is used in the well portion, the bearing 16 is secured to an edge 17 of the PCR microplate by bonding or screws. Alternatively, a part corresponding to the PCR microplate and the bearing 16 may be combined into a single unit.

The lid 13 is sized to cover a total of 24 wells in 12 rows of the wells 4 and 5 only, and has the same size as that of a heating block described below.

A thermal cycling block 18 in the thermal cycling unit is made of metal with high heat conductivity, such as aluminum or copper alloy, and is provided with 24 wells (holes).

Peltier devices 19 for heating the thermal cycling block 18 are disposed under the thermal cycling block 18. Grease (not shown) is provided between the thermal cycling block 18 and the Peltier devices 19 to ensure perfect contact therebetween, and thus to achieve reliable heat transfer. A sheet having high heat conductivity may be provided in place of the grease to achieve a similar effect.

The number of the Peltier devices 19 is determined such that all the wells in 12 rows in the container 3 are uniformly heated.

The wells 4 and 5 are disposed opposite the thermal cycling block 18. As for the dimensions, the outer walls of the wells 4 and 5 are in close contact with the corresponding inner walls of the thermal cycling block 18.

The thermal cycling block 18 is covered with a thermal insulator (not shown) made of resin so as to retain heat therein.

A magnet 20 and a magnet supporting member 21 are provided between the wells 6 and 7 and moved to a position 23 for collecting magnetic particles in the purification step. A total of 12 magnets 20 and 12 magnet supporting members 21 corresponding to respective well rows are pivotally supported by a magnet rotating shaft 22. The magnet rotating shaft 22 is supported by a bearing unit (not shown) in a retaining plate 32 described below. Each magnet supporting member 21 is connected to a solenoid (not shown) at one end opposite the magnet 20. To attract magnetic particles to the wall surface of the corresponding well, current is applied to the solenoid to draw in the magnet supporting member 21 and allow the magnet 20 to rise to the position 23.

A cooling block 24 in the cold reserving unit is made of metal with high heat conductivity, such as aluminum or copper alloy, and is provided with 48 wells (holes).

Peltier devices 25 for cooling the cooling block 24 are disposed under the cooling block 24. Grease (not shown) is provided between the cooling block 24 and the Peltier devices 25 to ensure perfect contact therebetween, and thus to achieve reliable heat transfer. A sheet having high heat conductivity may be provided in place of the grease to achieve a similar effect.

The number of the Peltier devices 25 is determined such that all the wells in 12 rows in the container 3 are uniformly cooled.

The wells 8 through 11 are disposed opposite the cooling block 24. As for the dimensions, the outer walls of the wells 8 through 11 are in close contact with the corresponding inner walls of the cooling block 24.

The cooling block 24 is covered with a thermal insulator (not shown) made of resin so as not to be significantly affected by ambient temperature.

A top plate unit 26 heats the container 3 from above. A heating block 27 made of aluminum or copper alloy is sized to cover the wells 4 and 5 only, and is configured not to heat the wells 6 through 11. Peltier devices 28 are disposed over the heating block 27. Grease (not shown) is provided between the heating block 27 and the Peltier devices 28 so as to ensure perfect contact therebetween, and thus to achieve reliable heat transfer.

A cooling block 29 made of metal is disposed over the Peltier devices 28. Again, to ensure perfect contact, the cooling block 29 is secured to the Peltier devices 28 with grease provided therebetween. When the Peltier devices 28 dissipate heat from the rear thereof, the cooling block 29 facilitates cooling.

The cooling block 29 is hollow and has a port connected to a pipe (not shown) through which coolant flows.

A retaining member 30 has an opening 31 on the upper surface, retains the heating block 27, the Peltier devices 28, and the cooling block 29, and serves as a thermal insulator.

The heating block 27, the Peltier devices 28, the cooling block 29, and the retaining member 30 constitute a single unit (top plate unit 26), which is movable to the right in the drawing.

The top plate unit 26 is configured to have a width that allows all the wells in 12 rows in the container 3 to be uniformly heated.

The top plate unit 26 is in close contact with the wells 4 and 5 during amplification, and heats these wells from above.

FIGS. 8A, 8B, 9A, and 9B illustrate components which specifically involve the opening and closing of the top plate unit 26 and lid 13.

Figure 8A:
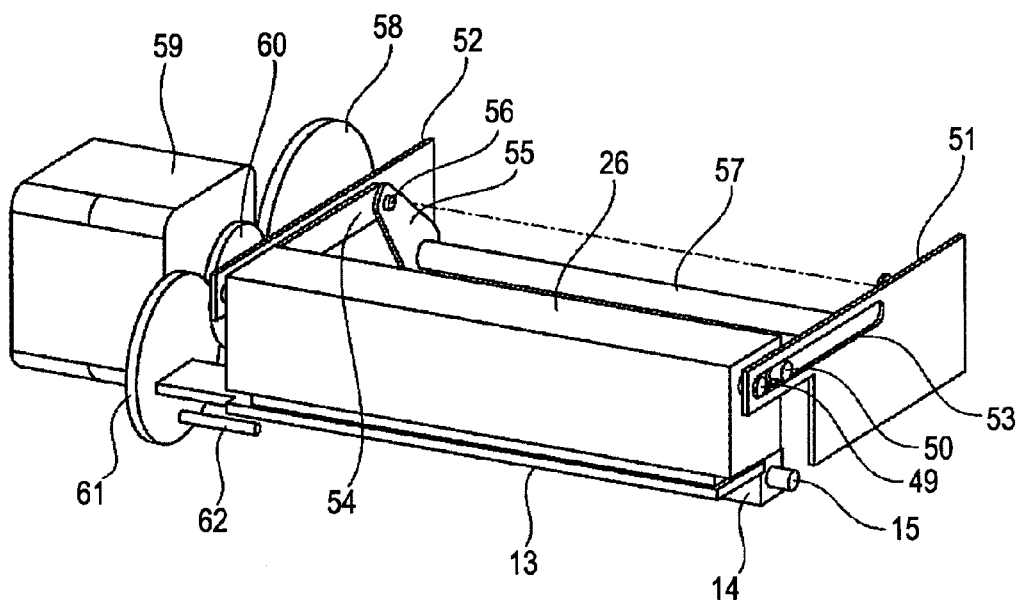
FIG. 8A and FIG. 8B illustrate a top plate unit and a lid drive mechanism of the present invention.
Figure 8B:
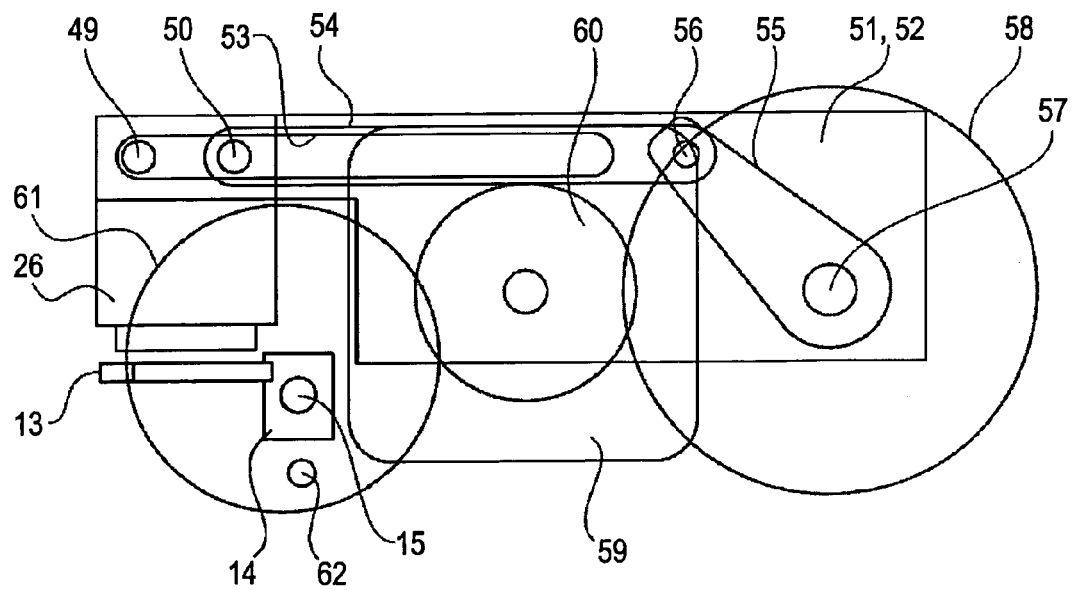

FIGS. 8A and 8B illustrate a state in which the top plate unit 26 is located directly above and at a distance from the lid 13. FIGS. 8A and 8B illustrate the same state as that in FIG. 5. FIG. 8A is a perspective view and FIG. 8B is a transparent view of all components as viewed from the right side of FIG. 8A.

In FIGS. 8A and 8B, pins 49 and 50 are secured to both sides of the top plate unit 26. Side plates 51 and 52 are disposed on respective sides of the top plate unit 26 and secured to the main body of the apparatus (the secured portions are not shown). The side plate 51 is provided with a slot 53, which is also provided in the side plate 52. The pins 49 and 50 are slidable in each slot 53. Links 54 are also provided on the respective sides of the top plate unit 26. Each link 54 is pivotally supported by the pin 50 at one end. Links 55 are also provided on the respective sides of the top plate unit 26. Each link 55 is pivotally supported by a pin 56 at one end. The links 55 are attached to respective ends of a top-plate drive shaft 57. A gear 58 is attached to one end of the top-plate drive shaft 57. A gear 60 is attached to one end of a motor 59, which transmits power to the gear 58 and to a gear 61. A shaft 62 is secured to the gear 61 and opens and closes the lid 13. The shaft 62 is positioned to overlap the lid 13. A retaining unit for the motor 59 and gears 58, 60, and 61 is omitted in FIGS. 8A and 8B.

Figure 9A:
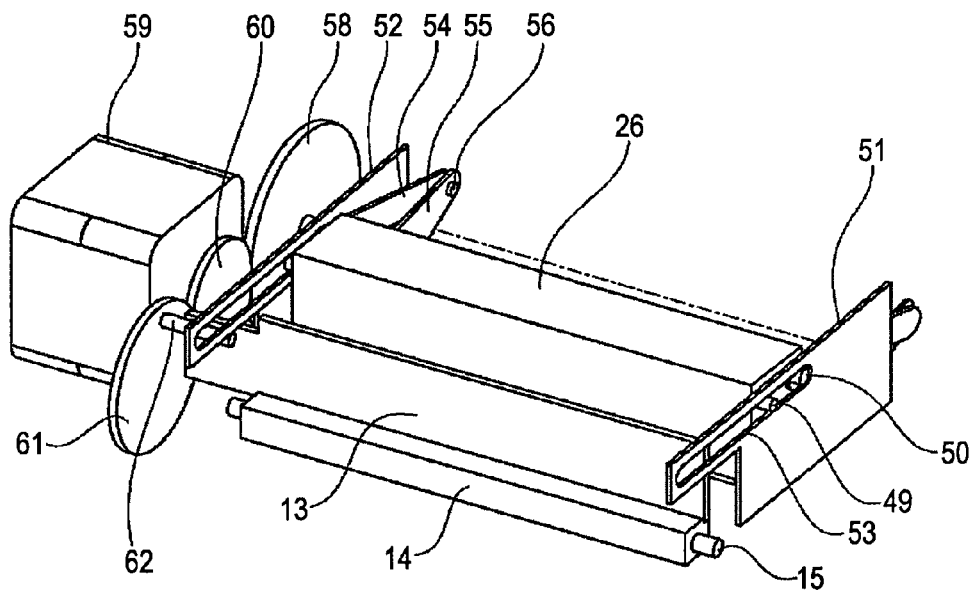
FIG. 9A and FIG. 9B illustrate the top plate unit and the lid drive mechanism of the present invention.
Figure 9B:
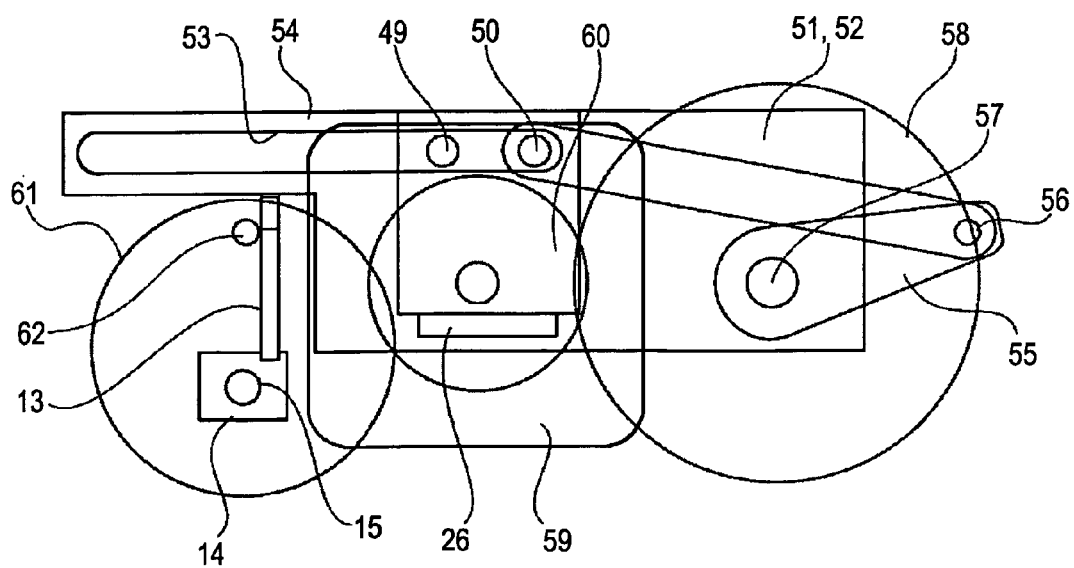

FIGS. 9A and 9B illustrate a state in which the top plate unit 26 is moved away to allow the lid 13 to be opened. FIGS. 9A and 9B illustrate the same state as that in FIG. 6. FIG. 9A is a perspective view and FIG. 9B is a transparent view of all components as viewed from the right side of FIG. 9A.

A transition from the state illustrated in FIGS. 8A and 8B to the state illustrated in FIGS. 9A and 9B will be described. Driving the motor 59 in the counterclockwise direction in FIG. 8B causes the gear 58 and top-plate drive shaft 57 to rotate clockwise via the gear 60 and causes the link 55 to pivot clockwise about the top-plate drive shaft 57. This drives the link 54 and causes the pins 49 and 50, via the pin 56 engaged with one end of the link 54, to slide along the slot 53, that is, causes the top plate unit 26 to move to the right.

Simultaneously with the rotation of the gear 58, the gear 61 rotates clockwise and brings the shaft 62 into contact with an end of the lid 13. The gear 61 continues rotating and causes the lid 13 to move about the fulcrum shaft 15. When the lid 13 reaches a position illustrated in FIGS. 9A and 9B, a sensor (not shown) detects the position and stops the driving of the motor 59. If the motor 59 is driven clockwise at this point, the lid 13 rotates in the closing direction. Then, when a home position sensor (not shown) detects that the lid 13 has reached the stop position (illustrated in FIGS. 8A and 8B), the driving of the motor 59 is stopped.

To avoid interference between operations, the lid 13 does not start opening until after the top plate unit 26 has moved away to some extent, and when the top plate unit 26 has reached near the home position, the lid 13 has already closed.

Figure 5:
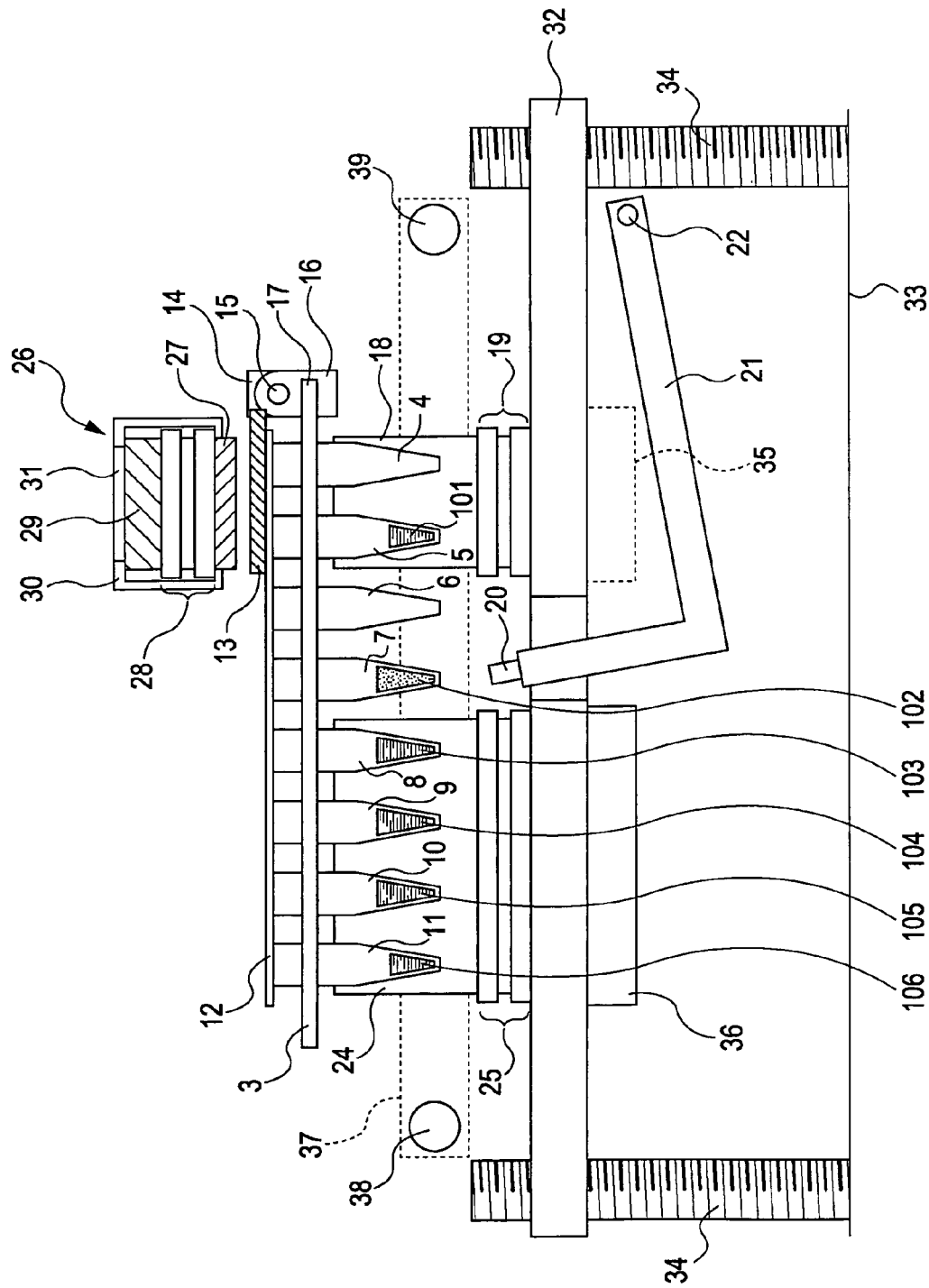
FIG. 5 is a front view illustrating the amplification unit of the DNA testing apparatus of the present invention and illustrates a state before the start of amplification.
Figure 6:
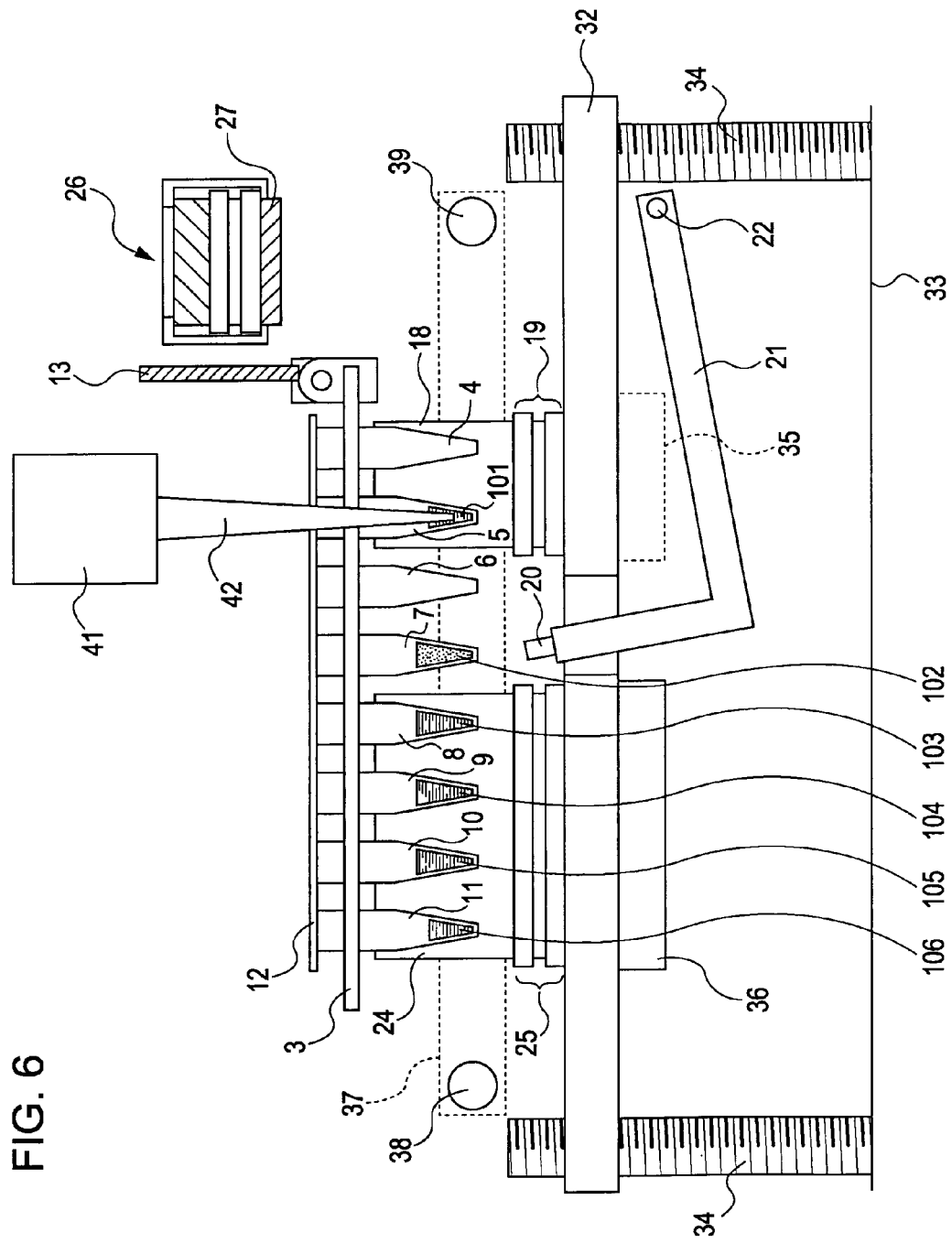
FIG. 6 is a front view illustrating the amplification unit of the DNA testing apparatus of the present invention and illustrates a state in which nucleic acid solution is injected.

Referring to FIGS. 5 and 6, since the thermal cycling block 18 and the cooling block 24 are engaged with the container 3, raising the retaining plate 32 (described below) causes the container 3 to be pressed against the top plate unit 26. This ensures better contact of the outer surfaces of the wells with the thermal cycling block 18 and cooling block 24, and thus improves heat conductivity to the wells.

The retaining plate 32 for retaining the thermal cycling unit, cold reserving unit, and purifying unit is disposed under the Peltier devices 19 and 25. The retaining plate 32 and the components thereon are integrally and vertically (in FIGS. 5 and 6) driven by lead screws 34 supported by bearings (not shown) on a base 33 of the apparatus, and by a motor and drive transfer system (not shown).

Water-cooling blocks 35 and 36 made of metal are secured to the under surface of the retaining plate 32 with grease provided between the retaining plate 32 and the water-cooling blocks 35 and 36. The water-cooling blocks 35 and 36 are disposed opposite the Peltier devices 19 and 25, respectively, with the retaining plate 32 interposed. The water-cooling blocks 35 and 36 facilitate the cooling of the Peltier devices 19 and 25 from the under surfaces of the Peltier devices 19 and 25. The water-cooling block 35 under the Peltier devices 19 is positioned so as not to interfere with the magnet supporting member 21. The water-cooling block 35 is indicated by a dotted line in the drawings.

The water-cooling blocks 35 and 36 are hollow and each has a port connected to a pipe (not shown) through which coolant flows.

The container 3 is attached to a carriage 37 indicated by a dotted line in the drawings. A lead screw 38 and a guide shaft 39 are disposed in the direction perpendicular to the plane of the drawings. Through the motor and drive transfer system (not shown), the carriage 37 is driven back and forth by the lead screw 38 and guide shaft 39. The height of the carriage 37 is a height at which the container 3 is attached thereto. The container 3 is attached to the carriage 37 when the carriage 37 is located at the front of the apparatus. The carriage 37 is driven to the rear of the apparatus and stopped when the container 3 reaches the position opposite the thermal cycling unit, cold reserving unit, and purifying unit. When the carriage 37 is stopped, the retaining plate 32 is located lower than that illustrated in FIG. 3 and does not interfere with the container 3. After that, the lead screws 34 raise the retaining plate 32 to the position illustrated in FIG. 3.

Next, the operation of the DNA testing apparatus will be described. Although the following description refers only to the operation in one well row (for one sample), the operation in the other rows is performed in the same manner.

Figure 4:
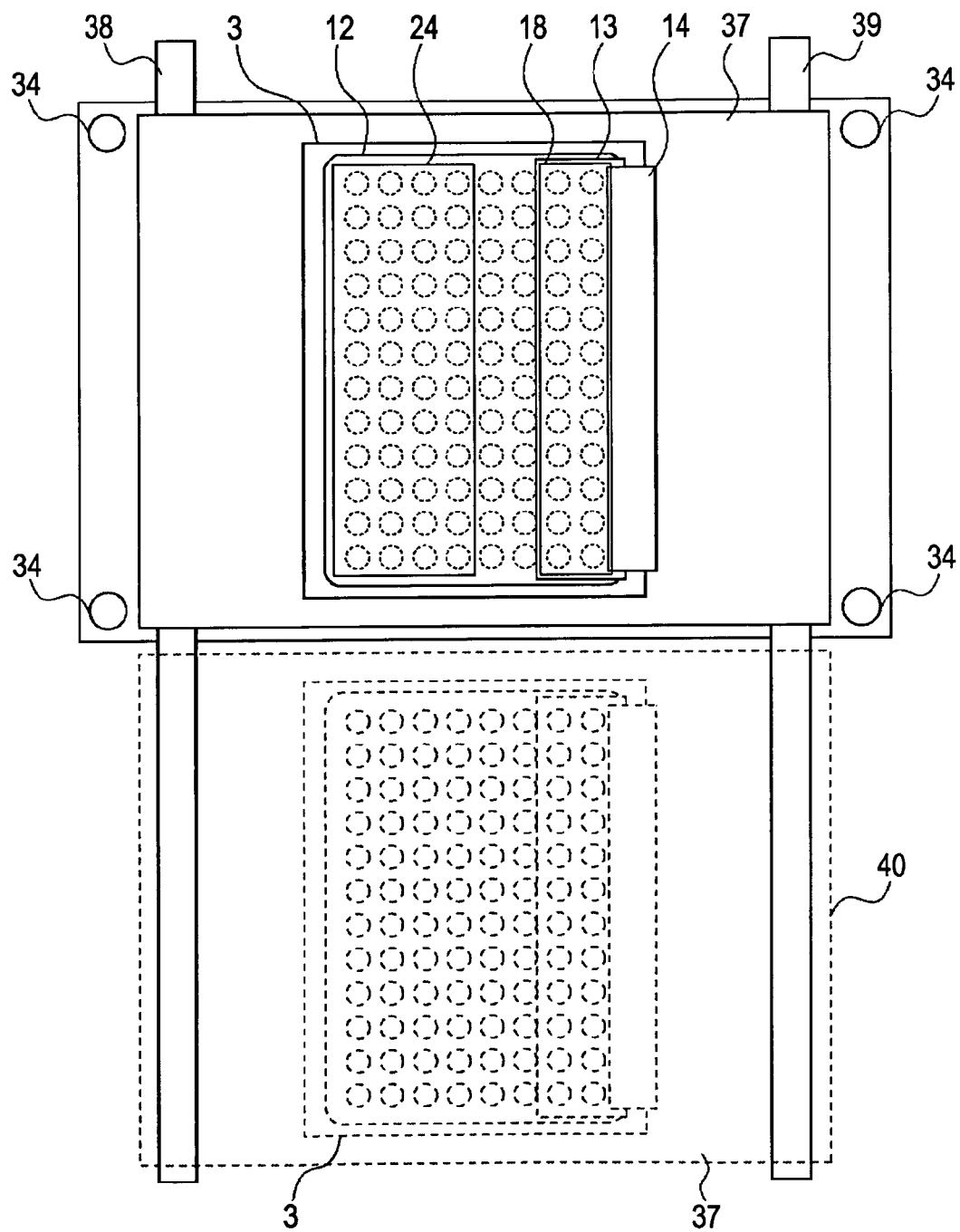
FIG. 4 is a top view illustrating the amplification unit of the DNA testing apparatus of the present invention.

FIG. 4 is a top view of FIG. 3 and illustrates major components of the DNA testing apparatus except the top plate unit 26 and the like.

When the user attaches the container 3 to the carriage 37 located at a position indicated by dotted line 40, the container 3 is transported rearward (upward in FIG. 4) by a drive motor (not shown) and the lead screw 38. When the container 3 reaches a position indicated by a solid line, the lead screws 34 raise the retaining plate 32 to the position illustrated in FIG. 5. The retaining plate 32 illustrated in FIG. 5 is located at a position slightly lower than that in FIG. 3. In FIG. 5, the heating block 27 is not in contact with the lid 13.

Solution containing nucleic acid extracted from a biological sample, such as blood or urine, in the extraction step performed by the extraction unit 202 in FIG. 1 is transferred with a pipette into the well 5.

FIG. 6 illustrates a state in which nucleic acid solution is injected with a pipette into the well 5.

A pipette unit 41 transfers, injects, and stirs solution through a pipette tip 42 removably attached to an end of the pipette unit 41. The pipette unit 41 is configured to be moved up/down, back/forth, and left/right by a pipette transport unit (not shown) including a motor and a lead screw.

A cutter unit (not shown) for piercing a film which hermetically seals the wells is provided to the right (in the drawing) of the pipette tip 42. Additionally, a pipette holder unit (not shown) for holding a pipette tip to be used and a pipette discarding unit (not shown) for holding a used pipette tip are also provided near the pipette tip 42. The cutter unit is transported to a predetermined position by the pipette transport unit. The film 12 is pierced in advance by the cutter unit at a point opposite the well 5. This allows the pipette tip 42 to be inserted into the well 5.

Before the film 12 is pierced, the top plate unit 26 is moved to the right and the lid 13 is rotated about 90 degrees by a drive mechanism (not shown) so that the wells 4 and 5 are opened.

Nucleic acid solution in the extraction unit located on the right side of FIG. 6 is drawn into the pipette tip 42, which is transferred to a position above the well 5. Then, the pipette tip 42 is inserted downward into the well 5 until a predetermined depth is reached. The nucleic acid solution is thus injected in the well 5.

Then, with the pipette tip 42 left inside the well 5, suction and injection are repeated a predetermined number of times so as to ensure sufficient mixing (stirring) of the nucleic acid solution with reagent placed in advance.

Upon completion of the mixing, the pipette unit 41 is moved away from above the container 3. The top plate unit 26 and the lid 13 are brought into a position to hermetically seal the wells 4 and 5 as illustrated in FIG. 5.

Then, the lead screws 34 raise the retaining plate 32 to the position shown in FIG. 3. Since the retaining plate 32 is thus biased against the top plate unit 26, the lid 13 is pressed by the wells with a force of 50 to 100 gf or above per well.

The first PCR starts in the state shown in FIG. 3. Temperatures of about 92° C., 55° C., and 72° C. are sequentially maintained for respective predetermined time periods within one cycle, which is repeated a predetermined number of times. This amplifies the nucleic acid in sample tubes. During the first PCR, the cold reserving unit is maintained at a temperature of, for example, about 4° C. which does not deteriorate reagents. Substantial parts of the thermal cycling unit (wells 4 and 5) and cold reserving unit (wells 8 through 11) are covered with the thermal insulator (not shown). Moreover, the purifying unit (wells 6 and 7) is disposed between the thermal cycling unit and the cold reserving unit. Therefore, a certain distance between the thermal cycling unit and the cold reserving unit is ensured. This arrangement prevents the temperatures of the thermal cycling unit and cold reserving unit from affecting each other.

After the completion of the first PCR, a purification step starts.

Figure 7:
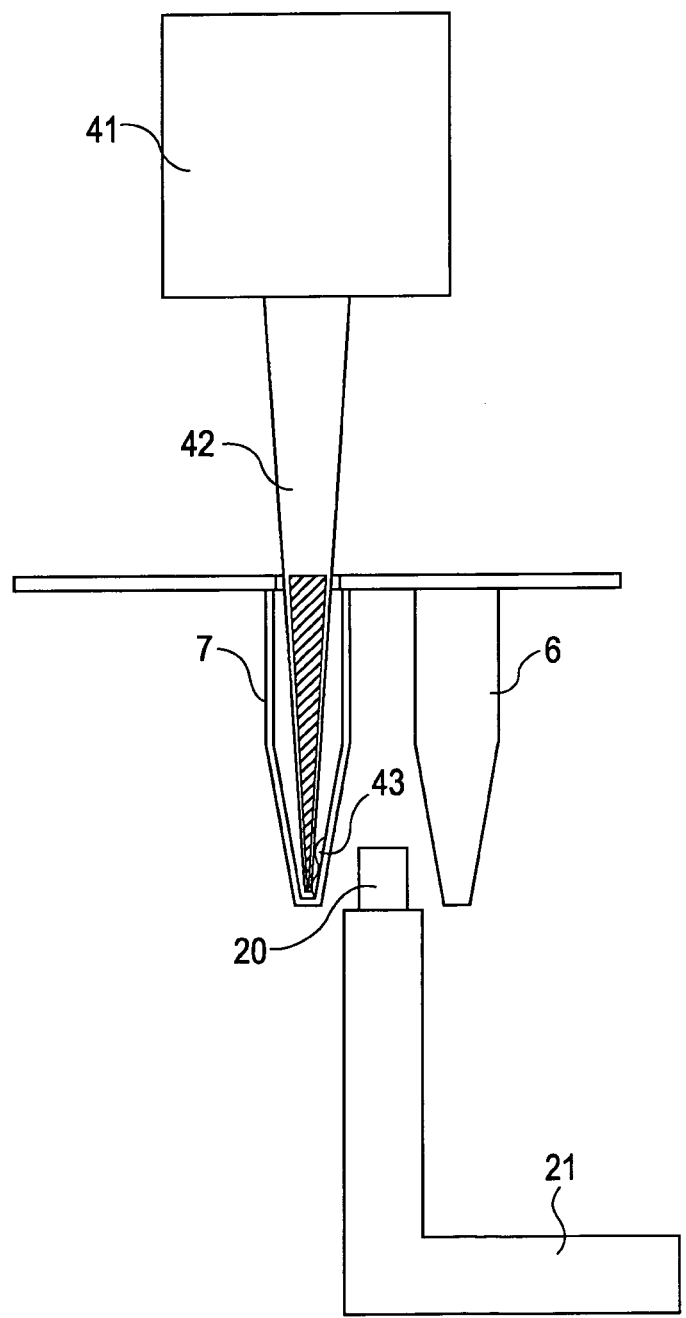
FIG. 7 illustrates a purification step of the present invention.

FIG. 7 illustrates a state in which, after the nucleic acid in the product of amplification is attracted to magnetic particles (hereinafter referred to as "nucleic acid magnetic particles 43") and collected by the magnet 20, the remaining solution is drawn into the pipette tip 42.

First, as illustrated in FIG. 6, the top plate unit 26 is moved away to allow the lid 13 to open. Then, solution in the well 5 is drawn into the pipette tip 42 and injected into the well 7. The film 12 on the well 7 has been pierced with the cutter unit in advance. Upon completion of the filling of the well 7, the top plate unit 26 and the lid 13 are returned to the previous position so that the wells 4 and 5 are hermetically sealed as illustrated in FIG. 5.

Next, the magnetic particle solution 102 filled in advance in the well 7 and the solution transferred from the well 5 are stirred by the pipette tip 42. After the nucleic acid is sufficiently attracted to the magnetic particles, the magnet 20 is raised to the position illustrated in FIG. 7 and allows the nucleic acid magnetic particles 43 to be collected to one place on the inner surface of the well 7. Then, a solution excluding the nucleic acid magnetic particles 43 is drawn into the pipette tip 42 as illustrated in FIG. 7, and discharged to a waste liquid treatment unit (not shown). The temperature of the thermal cycling block may be lowered to room temperature after the completion of the first PCR.

Next, the magnet 20 is moved away from the well 7. After the film 12 on the well 8 is pierced, the cleaning solution 103 is drawn and transferred from the well 8 to the well 7 and stirred by the pipette tip 42. Then, the magnet 20 is raised to allow the nucleic acid magnetic particles 43 to be collected at one place on the inner surface of the well 8. As in the case of FIG. 7, a solution excluding the nucleic acid magnetic particles 43 is drawn into the pipette tip 42 and discharged to the waste liquid treatment unit (not shown).

Likewise, after the ethanol 104 in the well 9 is transferred to the well 7, a solution excluding the nucleic acid magnetic particles 43 is drawn and discharged to the waste liquid treatment unit (not shown). A cleaning process in the purification step thus ends.

Then, the process proceeds to the last step of eluting nucleic acid from the nucleic acid magnetic particles 43.

The solution in the well 7 and eluate in the well 10 are transferred to the well 6, stirred, and left for a while, as in the case of the cleaning solution 103 and the ethanol 104. Then, magnetic particles are collected to one place by the magnet 20. The nucleic acid is isolated from the magnetic particles in the eluate. This solution is a nucleic acid solution produced through the process of purification. A predetermined amount of this nucleic acid solution is drawn from the well 6 (as in the case of FIG. 7) and transferred to the well 4. Before the transfer, the top plate unit 26 is moved away (as illustrated in FIG. 6) to allow the lid 13 to open, and the film 12 on the well 4 is pierced by the cutter unit. The purification step thus ends.

Next, after the film 12 on the well 11 is pierced, the solution 106 to be used in the second PCR is transferred to the well 4 and stirred with the pipette tip 42. After the stirring, the lid 13 is positioned to hermetically seal the wells 4 and 5 as illustrated in FIG. 5. Subsequently, the heating block 27 is brought into close contact with the lid 13 as illustrated in FIG. 3 and the second PCR starts. Since all reagents have already been used up, cooling of the cooling block 24 may be stopped during the second PCR.

Upon completion of the second PCR, the top plate unit 26 is moved away as illustrated in FIG. 6 to allow the lid 13 to open. Then, the product of amplification is transferred from the well 5 to the hybridization unit (not shown) by the pipette tip 42. After the transfer, when the state of FIG. 3 is restored and the retaining plate 32 is lowered to transport the carriage 37 forward, the container 3 becomes removable from the DNA testing apparatus.

As described above, throughout the processes of the first PCR, purification, and second PCR, the lid 13 is opened and closed every time the film 12 on the wells 4 and 5 is pierced, and solution is drawn from or injected into the wells 4 and 5. Since the wells 4 and 5 are opened and closed multiple times, the lid 13 is not of a piercing type but of an opening and closing type.

The operation of moving the top plate unit 26 away and back is performed simultaneously with the opening and closing of the lid 13 by a single drive source (while there is practically a time difference between the operations of the top plate unit 26 and lid 13, as a certain amount of time elapses from when the top plate unit 26 starts moving away until the lid 13 starts moving). Therefore, the lid 13 can be opened and closed quickly and thus a time period during which the wells 4 and 5 are exposed to the outside can be reduced.

When the amplification and purification steps are completed and the container 3 is returned to the position indicated by dotted line 40 in FIG. 4, the container 3 becomes removable from the apparatus. Since the lid 13 is integral with the container 3, the lid 13 and the container 3 can be discarded together, which contributes to the ease of waste handling.

As described with reference to FIG. 3, solutions are placed in advance in the container 3 in order of use. With this arrangement, the pipette tip containing solution is prevented as far as possible from passing over unused (sealed) wells. Even if solution is dropped from the pipette tip, it is unlikely that it is dropped onto the unused wells. Therefore, the amplification and purification steps are not affected.

Second Exemplary Embodiment

In the first exemplary embodiment described above, a single motor simultaneously drives the top plate unit 26 and the lid 13 so as to reduce the operating time. However, a mechanism for driving the top plate unit 26 and lid 13 is not limited to this. For example, in FIGS. 8A and 8B and FIGS. 9A and 9B, the gear 58 and the gear 61 may be driven by their respective motors to operate the top plate unit 26 and lid 13.

Although the torsion coil spring biases the lid 13 in a direction to hermetically seal the wells 4 and 5 in the first exemplary embodiment, other methods may also be used. For example, an iron member is provided near the lid 13 and opposite the magnet so that the wells 4 and 5 are normally sealed by a magnetic force. For opening the lid 13 in this case, a means for isolating the lid 13 against the magnetic force needs to be provided on the apparatus.

The present invention is achieved by various known mechanisms and is not limited to a specific mechanism.

Third Exemplary Embodiment

Although reagents only for the amplification step are placed in the container 3 in the embodiments described above, regents for other steps (i.e., extraction, hybridization, and detection) may be placed together.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

What is claimed is:

1. A biochemical processing apparatus for performing a plurality of biochemical processings in a container provided with a plurality of wells, comprising:
   a retainer configured to retain the container;
   a pipette unit configured to be movable to the container;
   a heating/cooling unit configured to selectively heat or cool a liquid in a first group of the plurality of wells independent of another group of the plurality of wells; and
   a lid capable of hermetically sealing the first group of the plurality of wells, the lid being opened or closed by being rotated about a rotation axis,
   wherein the heating/cooling unit heats the liquid in the first group of the plurality of wells while the lid seals the first group of the plurality of wells near the rotation axis without sealing the other group of the plurality of wells.

2. The biochemical processing apparatus according to claim 1, wherein the container provided with the plurality of wells is a well plate, and wherein the lid covers the first group of the plurality of wells in two rows of the well plate, the two rows being near the rotation axis of the lid.

3. The biochemical processing apparatus according to claim 1, further comprising a cold reserving unit.

4. The biochemical processing apparatus according to claim 1, further comprising a purifying unit.

5. The biochemical processing apparatus according to claim 1, further comprising a cold reserving unit and a purifying unit, wherein the cold reserving unit, the purifying unit and the heating/cooling unit are disposed in this order.

6. The biochemical processing apparatus according to claim 1, wherein the container is provided with the plurality of wells integrally.

* * * * *